(12) United States Patent
Razavi et al.

(10) Patent No.: US 9,314,191 B2
(45) Date of Patent: Apr. 19, 2016

(54) METHOD AND SYSTEM TO MEASURE CARDIAC MOTION USING A CARDIOVASCULAR NAVIGATION SYSTEM

(71) Applicant: Pacesetter, inc., Sunnyvale, CA (US)

(72) Inventors: Hoda Razavi, San Jose, CA (US); Yelena Nabutovsky, Mountain View, CA (US); Kyungmoo Ryu, Palmdale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 66 days.

(21) Appl. No.: 14/328,513

(22) Filed: Jul. 10, 2014

(65) Prior Publication Data

US 2015/0141858 A1    May 21, 2015

Related U.S. Application Data

(60) Provisional application No. 61/906,300, filed on Nov. 19, 2013, provisional application No. 61/906,305, filed on Nov. 19, 2013.

(51) Int. Cl.
*A61B 5/11* (2006.01)
*A61B 6/00* (2006.01)
(Continued)

(52) U.S. Cl.
CPC ............. *A61B 5/1107* (2013.01); *A61B 5/042* (2013.01); *A61B 5/062* (2013.01); *A61B 5/066* (2013.01);
(Continued)

(58) Field of Classification Search
CPC .... A61B 5/1107; A61B 5/721; A61B 5/1122; A61B 5/1114; A61B 5/066; A61B 6/527; A61B 5/042; A61B 5/062; A61B 5/7289; A61B 5/1128; A61B 6/4441; A61B 6/501; A61B 6/469; A61B 6/487; A61B 6/5288
See application file for complete search history.

(56) References Cited

U.S. PATENT DOCUMENTS

| 5,391,199 A | 2/1995 | Ben-Haim |
| 6,233,476 B1 | 5/2001 | Strommer et al. |

(Continued)

FOREIGN PATENT DOCUMENTS

| EP | 1 070 480 A2 | 1/2001 |
| EP | 1 508 300 A1 | 2/2005 |

(Continued)

OTHER PUBLICATIONS

Notice of Allowance mailed Oct. 27, 2015; Related U.S. Appl. No. 14/328,523.

(Continued)

*Primary Examiner* — Rex R Holmes
(74) *Attorney, Agent, or Firm* — Theresa A. Raymer

(57) ABSTRACT

A method and system are provided to measure cardiac motion data using a cardiovascular navigation system. The method and system position a patient reference sensor (PRS) on a patient, wherein the PRS determines a position of the patient relative to a reference point. The method and system determine a reference orientation matrix based on an orientation of the PRS relative to a reference point and determining a normalization time based on an electrical signal. The method and system obtain point specific (PS) motion data for a plurality of map points. The PS motion data indicates a three dimensional trajectory that occurs at the corresponding map point on a wall of a heart of the patient during at least one cardiac cycle. Further the method and system compensate the PS motion data based on the PRS.

20 Claims, 9 Drawing Sheets

(51) Int. Cl.
  *A61B 5/042* (2006.01)
  *A61B 5/06* (2006.01)
  *A61B 5/0452* (2006.01)
  *A61B 5/00* (2006.01)
  *A61B 5/04* (2006.01)
  *A61B 5/113* (2006.01)
  *A61B 19/00* (2006.01)

(52) U.S. Cl.
  CPC .............. *A61B 5/1114* (2013.01); *A61B 5/1122* (2013.01); *A61B 5/1128* (2013.01); *A61B 5/721* (2013.01); *A61B 5/7289* (2013.01); *A61B 6/527* (2013.01); *A61B 5/04014* (2013.01); *A61B 5/0452* (2013.01); *A61B 5/113* (2013.01); *A61B 5/6852* (2013.01); *A61B 5/6869* (2013.01); *A61B 5/7435* (2013.01); *A61B 6/4441* (2013.01); *A61B 6/469* (2013.01); *A61B 6/487* (2013.01); *A61B 6/501* (2013.01); *A61B 6/5288* (2013.01); *A61B 2019/507* (2013.01); *A61B 2019/5483* (2013.01)

(56) References Cited

U.S. PATENT DOCUMENTS

| | | |
|---|---|---|
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 2003/0093067 A1 | 5/2003 | Panescu |
| 2003/0233039 A1 | 12/2003 | Shao et al. |
| 2005/0154282 A1 | 7/2005 | Li et al. |
| 2006/0245536 A1 | 11/2006 | Boing |
| 2007/0073179 A1 | 3/2007 | Afonso et al. |
| 2007/0100332 A1 | 5/2007 | Paul et al. |
| 2007/0106146 A1 | 5/2007 | Altmann et al. |
| 2007/0181139 A1 | 8/2007 | Hauck |
| 2007/0244479 A1 | 10/2007 | Beatty et al. |
| 2007/0270705 A1 | 11/2007 | Starks |
| 2008/0009758 A1 | 1/2008 | Voth |
| 2008/0091193 A1 | 4/2008 | Kauphusman et al. |
| 2009/0163904 A1 | 6/2009 | Miller et al. |
| 2009/0171345 A1 | 7/2009 | Miller et al. |
| 2010/0168550 A1 | 7/2010 | Byrd et al. |
| 2010/0268059 A1 | 10/2010 | Ryu |
| 2011/0243401 A1 | 10/2011 | Zabair et al. |
| 2012/0184863 A1 | 7/2012 | Harlev et al. |
| 2013/0222415 A1 | 8/2013 | Vilsmeier |
| 2013/0272592 A1 | 10/2013 | Eichler et al. |
| 2015/0045867 A1 | 2/2015 | Krishnan et al. |
| 2015/0133802 A1 | 5/2015 | Nabutovsky et al. |
| 2015/0141765 A1 | 5/2015 | Razavi et al. |

FOREIGN PATENT DOCUMENTS

| | | |
|---|---|---|
| EP | 2 757 528 A1 | 7/2014 |
| WO | 97/24981 | 7/1997 |
| WO | 2012/090148 A1 | 7/2012 |

OTHER PUBLICATIONS

Notice of Allowance mailed Jun. 21, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action mailed Aug. 10, 2015; Related U.S. Appl. No. 12/347,216.
Amendment filed Jun. 25, 2015; Related U.S. Appl. No. 12/347,216.
Final Office Action mailed May 4, 2015; Related U.S. Appl. No. 12/347,216.
Amendment filed Dec. 18, 2014; Related U.S. Appl. No. 12/347,216.
Non-Final Office Action mailed Oct. 2, 2014; Related U.S. Appl. No. 12/347,216.
Advisory Action mailed May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action mailed Feb. 25, 2014; Related U.S. Appl. No. 12/347,216.
Amendment filed Feb. 4, 2014; Related U.S Appl. No. 12/347,216.
Non-Final Office Action mailed Nov. 21, 2013; Related U.S. Appl. No. 12/347,216.
Amendment filed Oct. 29, 2012; Related U.S. Appl. No. 12/347,216.
Advisory Action mailed Oct. 11, 2012; Related U.S. Appl. No. 12/347,216.
Amendment filed Oct. 1, 2012; Related U.S. Appl. No. 12/347,216.
Advisory Action mailed Sep. 12, 2012; Related U.S. Appl. No. 12/347,216.
Amendment filed Aug. 28, 2012; Related U.S. Appl. No. 12/347,216.
Final Office Action mailed Jun. 29, 2012; Related U.S. Appl. No. 12/347,216.
Amendment filed May 14, 2012; Related U.S. Appl. No. 12/347,216.
Interview Summary, Feb. 28, 2012; Related U.S. Appl. No. 12/347,216.
Non-Final Office Action mailed Feb. 13, 2012; Related U.S. Appl. No. 12/347,216.
Non-Final Office Action mailed Dec. 11, 2015; Related U.S. Appl. No. 14/703,460.
Non-Final Office Action mailed Sep. 30, 2015; Related U.S. Appl. No. 14/270,181.
Notice of Allowance mailed Dec. 8, 2015; Related U.S. Appl. No. 12/347,216.
Final Office Action mailed Jan. 22, 2016; Related U.S. Appl. No. 14/270,176.
Non-Final Office Action mailed Feb. 8, 2016; Related U.S. Appl. No. 14/270,181.

METHOD AND SYSTEM TO MEASURE CARDIAC MOTION USING A CARDIOVASCULAR NAVIGATION SYSTEM

RELATED APPLICATION DATA

The present application is related to and claims priority from the following applications: U.S. provisional application Ser. No. 61/906,300, filed Nov. 19, 2013, titled "METHOD TO MEASURE CARDIAC MOTION USING A CARDIOVASCULAR NAVIGATION SYSTEM", and U.S. provisional application Ser. No. 61/906,305, filed Nov. 19, 2013, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION," which is expressly incorporated herein by reference in their entirety in the present application.

BACKGROUND OF THE INVENTION

Embodiments of the present invention generally relate to measuring cardiac motion, and more particularly to measuring cardiac motion using a cardiovascular navigation system.

Cardiovascular navigation systems (CNS) provide real-time position and orientation information in relation to a part of the cardiovascular system, such as, the heart based on sensors placed at various locations within the cardiovascular system. The CNS may be integrated with a fluoroscopic (or other diagnostic) imaging system and track the sensors continuously within an imaging volume defined by the fluoroscopic system, on both live and recorded background diagnostic images.

Recently, it has been proposed to utilize the CNS to evaluate the motion of the heart and identify a desired (e.g., optimal) location for placement of a left ventricular (LV) lead in a cardiac resynchronization therapy (CRT) system. For example, the CNS may systematically record information, such as displacement of the sensors, associated with various endocardial and/or epicardial locations of the LV. Epicardial locations may include mapping within the coronary sinus branches as well as mapping directly on the epicardial surface of the LV via a sub-xiphoid puncture technique, for example.

However, the position and orientation data acquired by the cardiovascular navigation system is affected by the movement of the patient, translation of the patient table, measurement errors of the system, and the orientation and location of the CNS transmitters that may be integrated with the imaging system such as the fluoroscopic system. A need remains for methods and systems that can obtain motion data from a navigation system to assess cardiac motion.

SUMMARY

In accordance with embodiments herein, a method is provided to measure cardiac motion data using a cardiovascular navigation system. The method includes positioning a patient reference sensor (PRS) on a patient, wherein the PRS determines a position of the patient relative to a reference point. The method further includes determining a reference orientation matrix based on an orientation of the PRS relative to a reference point and determining a normalization time based on an electrical signal. The method obtains point specific (PS) motion data for a plurality of map points. The PS motion data indicates a three dimensional (3D) trajectory at the corresponding map point on a wall of a heart of the patient during at least one cardiac cycle. Further the method compensates the PS motion data based on the PRS.

Optionally, the method may include applying a rotation technique to a motion waveform for the corresponding map point based on the normalization time. The motion waveform may be defined by the PS motion data. Additionally, the motion waveform may be an ensemble average based on PS motion data obtained during a plurality of cardiac cycles.

Optionally, the method may include converting the PS motion data into a cardiac coordinate system based on the patient-specific anatomy.

Optionally, the method may include applying a high-pass or band-stop filter to the PS motion data based on a respiratory frequency of the patient.

Optionally, the electrical signal may be a 12-lead surface ECG from the patient.

Optionally, the PS motion data may be obtained by an electrophysiological sensor.

Optionally, the normalization time may be based on a peak of the electric signal and at least one of an earliest global electrical activation or a predetermined percentage of a cycle length.

In an embodiment, a system for measuring cardiac motion is provided. The system includes a patient reference sensor (PRS) configured to determine a position of a patient relative to a reference point. The system includes a motion sensor configured to obtain point specific (PS) motion data for a plurality of map points. The PS motion data indicates a three dimensional (3D) trajectory at the corresponding map point on a wall of a heart of the patient during at least one cardiac cycle. The system also includes an input configured to receive the position measurements of the PRS and the motion sensor. The system includes a processor configured to determine a reference orientation matrix based on an orientation of the PRS relative to the reference point. The processor is also configured to determine a normalization time based on an electrical signal. The processor is further configured to compensate the PS motion data based on the PRS.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Embodiments herein may be implemented with, and/or utilize aspects of, the methods and system described in the following co-pending applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM"; U.S. provisional application Ser. No. 61/906,300, filed Nov. 19, 2013, titled "METHOD TO MEASURE CARDIAC MOTION USING A CARDIOVASCULAR NAVIGATION SYSTEM"; U.S. provisional application Ser. No. 61/906,305, filed Nov. 19, 2013, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION"; U.S. patent application Ser. No. 14/270,181, filed May 5, 2014, titled "METHOD AND SYSTEM TO CHARACTERIZE MOTION DATA BASED ON NEIGHBORING MAP POINTS"; U.S. patent application Ser. No. 14/270,176, filed May 5, 2014, titled "METHOD AND SYSTEM FOR DISPLAYING A THREE DIMENSIONAL VISUALIZATION OF CARDIAC MOTION"; and U.S. patent application Ser. No. 14/270,191, filed May 5, 2014, titled "METHOD AND SYSTEM TO AUTOMATICALLY ASSIGN MAP POINTS TO ANATOMICAL SEGMENTS", all of which are expressly incorporated herein by reference in their entirety.

Figure 1:
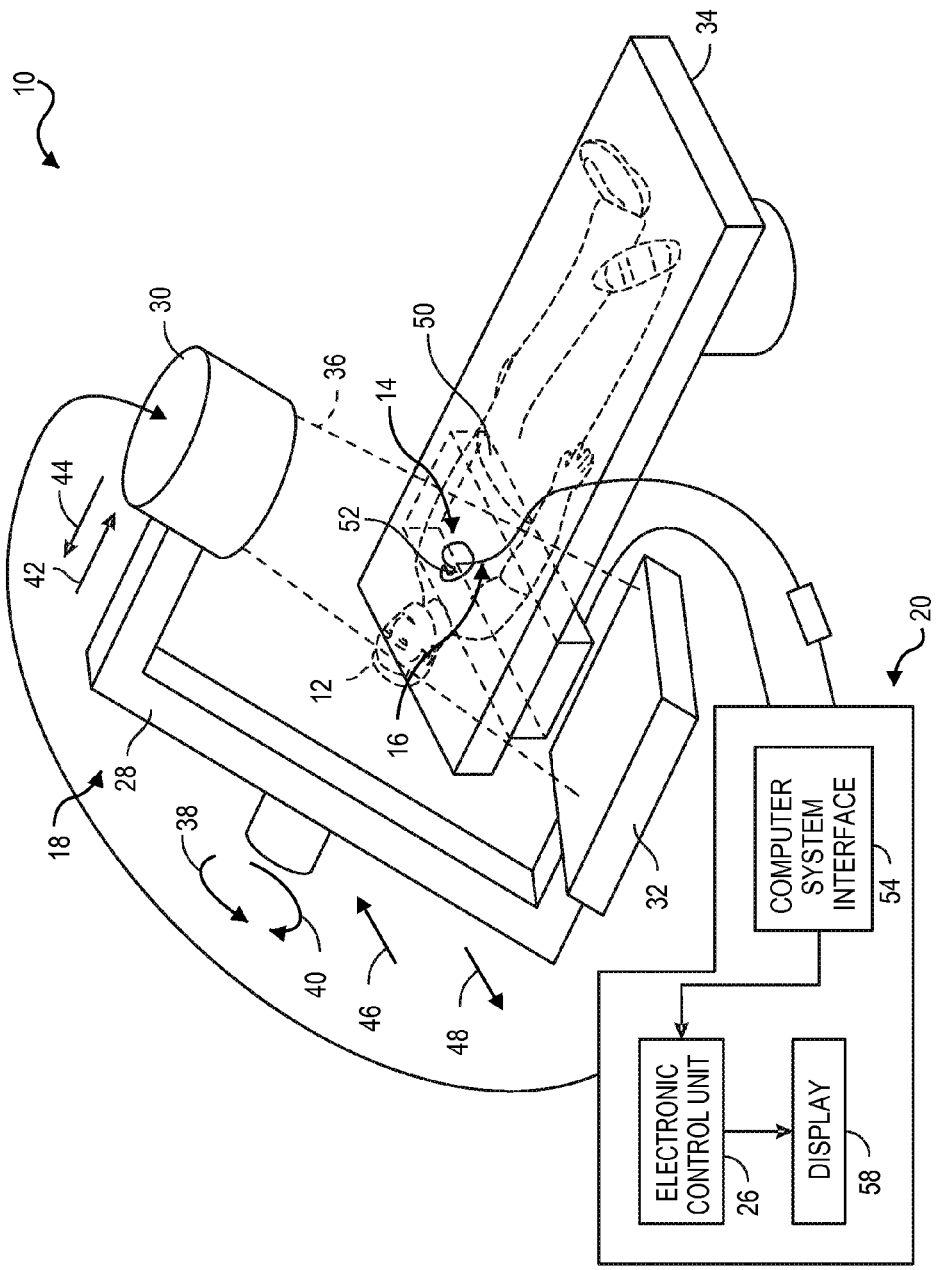
FIG. 1 illustrates a cardiovascular navigation system, in accordance with an embodiment herein.

FIG. 1 illustrates a cardiovascular navigation system (CNS) 10, of an embodiment, for use in imaging an anatomical region of a patient 12 such as a heart 14. A medical tool 16 is placed within the anatomical region, such as for example, an electrophysiological (EP) mapping catheter, a guidewire, and/or a catheter generally described or shown in U.S. Pat. No. 7,881,769, the entire disclosure of which is incorporated herein by reference. The medical tool 16 includes a plurality of electrophysiological sensors 52 that may be placed on the endocardial or epicardial surface of the cardiac chamber such as the left ventricle (LV) of the heart 14. The motion sensors 52 may be attached to the distal or proximal end of the medical tool 16, or any point in between. The motion sensors 52 transmit the position information to an electronic control unit (ECU) 26. For example, the motion sensors 52 may be positioned by the medical tool 16 to measure point specific (PS) motion data for a plurality of map points of the wall of the heart 14. It should be understood, however, that the motion sensors 52 could be used in a variety of anatomical regions within the heart 14 or other organs in which motion characterization may be of interest.

Additionally or alternatively, the motion sensors 52 may be used concurrently with electrical sensors. The electrical sensors may measure an electrical potential or an electric current of biological cells and tissues. Optionally, the ECU 26 may receive the PS motion data and electrical sensor measurements (e.g., electrical potential) concurrently from the motion sensors and electrical sensors. Optionally, the motion sensor 52 and the electrical sensor may be integrated to form an electrophysiological sensor.

Optionally, the CNS 10 may include an imaging system 18 and a medical device navigation system 20. The CNS 10 may further include a registration system for registering a group of images of the anatomical region of the patient 12 in a navigation coordinate system of the navigation system 20 as generally described and shown in U.S. Patent Publication 2013/0272592 and International Pub. No. WO 2012090148, the entire disclosure of which is incorporated herein by reference.

The imaging system 18 may be provided to acquire images of the heart 14 or another anatomical region of interest and comprises a fluoroscopic imaging system in the illustrated embodiment. Additionally or alternatively, rather than a fluoroscopic imaging system, computed tomography (CT) imaging systems, a three-dimensional rotational angiography (3DRA) system, and the like may be used. Although the imaging system 18 is described herein for an embodiment of the invention, the imaging system 18 is not required for the inventive subject matter described within this application The imaging system 18 may include a C-arm support structure 28, a radiation emitter 30, and a radiation detector 32. The emitter 30 and detector 32 are disposed on opposite ends of support structure 28 and disposed on opposite sides of the patient 12 as the patient 12 lays on an operation table 34. The emitter 30 and detector 32 define a field of view 36 and are positioned such that the field of view 36 includes the anatomical region of interest as the patient 12 lays on the operation table 34. The operation table 34 may be configured to move in a table up direction and a table down direction with respect to the emitter 30 or detector 32. Additionally or alternatively, the operation table 34 may be configured to move in an inward direction and an outward direction with respect to the C-arm support structure 28.

The imaging system 18 is configured to capture images of anatomical features and other objects within the field of view 36. The support structure 28 may have freedom to rotate about the patient as shown by lines 38, 40. Support structure 28 may also have freedom to slide along lines 42 and 44 (i.e. along the cranio-caudal axis of the patient 12) and/or along lines 46 and 48 (i.e. perpendicular to the cranio-caudal axis of the patient 12). Rotational and translational movement of support structure 28 yields corresponding rotational and translational movement of field of view 36.

The imaging system 18 may acquire a group of images of an anatomical region of the patient 12 by first shifting along lines 42, 44, 46, and/or 48 to place the anatomical region of interest within the field of view 36. Second, the support structure 28 may rotate the radiation emitter 30 and the radiation detector 32 about the patient 12, keeping the anatomical region within field of view 36. The imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

A navigation system 20 is provided to determine the position and orientation of the medical tool 16 within the body of the patient 12. In the illustrated embodiment, the navigation system 20 comprises a magnetic navigation system in which magnetic fields are generated in the anatomical region and position sensors associated with the medical tool 16 generate an output that changes responsive to the position of the sensors within the magnetic field. The navigation system 20 may comprise, for example, the systems generally shown and described in, for example, U.S. Pat. Nos. 6,233,476, 7,197,354, 7,386,339, and 7,505,809 all of which are incorporated by reference in their entirety. Although a magnetic navigation system is shown in the illustrated embodiment, it should be understood that the invention could find use with a variety of navigation systems including those based on the creation and detection of axes-specific electric fields. Additionally or alternatively, the navigation system 20 may be based on optical detection (e.g., videometric tracking, IR-based tracking, laser tracking).

The navigation system 20 may include a transmitter assembly 50. The transmitter assembly 50 may include a plurality of coils arranged orthogonally to one another to produce a magnetic field in and/or around the anatomical region of interest. It should be noted that, although the transmitter assembly 50 is shown under the body of the patient 12 and under the table 34 in FIG. 1, the transmitter assembly 50 may be placed in another location, such as attached to the radiation emitter 30 or detector 32, from which the magnetic field generators can project a magnetic field in the anatomical region of interest. In accordance with certain embodiments of the invention the transmitter assembly 50 is within the field of view 36. The ECU 26 may control the generation of magnetic fields by the transmitter assembly 50.

The motion sensors 52 are configured to generate an output dependent on the relative position of motion sensors 52 within the field generated by the transmitter assembly 50. In FIG. 1, the motion sensor 52 and the medical tool 16 are shown disposed around the heart 14. The navigation system 20 determines the location of the motion sensors 52 in the generated field, and thus the position of medical tool 16 as well. The navigation system 20 further may determine a navigation coordinates, such as a Cartesian coordinate (e.g., (X, Y, Z)), of the navigation coordinate system.

One or more patient reference sensors (not shown) are on the body of the patient 12, for example, on the chest. The patient reference sensors measure a displacement and orientation of the patient reference sensors relative to a predetermined reference point, such as, the motion sensors 52 or the transmitter assembly 50.

The ECU 26 of the navigation system 20 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by the medical tool 16, the imaging system 18, the motion sensors 52, an operator system interface 54 (e.g., keyboard, touchscreen, computer mouse, or the like), and the patient reference sensors (not shown) and generate a plurality of output signals including those used to control the medical tool 16, imaging system 18, and/or the display 58. The ECU 26 may also receive an input signal from an organ monitor (not shown), such as an ECG monitor, and sort or segregate images from the imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

Figure 2:
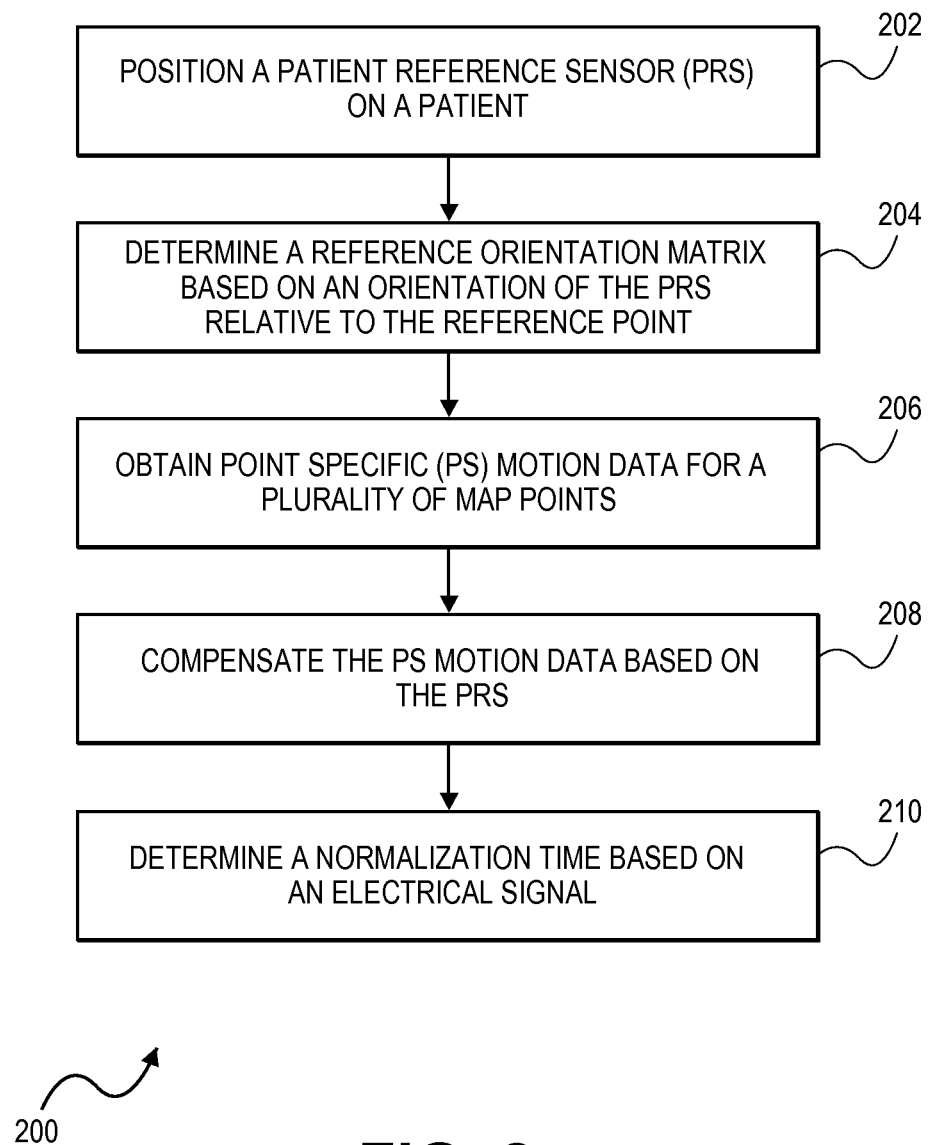
FIG. 2 is a flowchart of a method to measure cardiac motion using a cardiovascular navigation system, in accordance with an embodiment herein.

FIG. 2 illustrates a flowchart of a method 200 to measure cardiac motion using a CNS (e.g., 10). The method 200 may be implemented as a software algorithm, package, or system that directs one or more hardware circuits or circuitry to perform the actions described herein. For example, the operations of the method 200 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes i) positioning a patient reference sensor (PRS) on a patient, ii) determining a reference orientation matrix based on an orientation of the PRS relative to the reference point, iii) obtaining point specific (PS) motion data for a plurality of map points iv) compensating the PS motion data based on the PRS, and v) determining a normalization time based on an electrical signal.

Beginning at 202, the method 200 positions a patient reference sensor (PRS) on a patient. The PRS is positioned on the patient 12, such as the chest of the patient 12, to measure or detect any movement by the patient during the procedure.

At 204, the method 200 determines a reference orientation matrix based on an orientation of the PRS relative to the reference point. The reference sensors are positioned to determine a reference orientation of the reference sensors relative to the transmitter assembly 50 or c-arm support structure 28 to compensate for movement of the transmitter assembly 50 or the C-arm support structure 28 during the procedure. For example, in an embodiment of the system 10, the transmitter assembly 50 may be attached to the C-arm support structure 28. Movement of the C arm support structure 28 may affect the orientation of the PRS sensor, the position of which is referenced by the transmitter assembly 50. To compensate for the change in orientation, a reference orientation is calculated. At the beginning of the procedure, the imaging system 18 may output the orientation angle of the C-arm support structure 28 relative to the operation table 34 or any predetermined stationary reference to the navigation system 20. Once the reference sensors are placed, the navigation system 20 receives the reference sensor position relative to the transmitter assembly 50. The ECU 26 determines a reference orientation matrix representing the orientation of the reference sensors relative to the C-arm support structure 28 by transforming the position of the reference sensors using the fixed reference point, the operation table 34, to the orientation of the of the C-arm support structure 28.

At 206, the method 200 obtains point specific (PS) motion data for a plurality of map points. The motion sensors 52 are placed in contact with the wall of the heart 14 throughout at least one cardiac cycle. The position of the motion sensor 52 tracks the position of the wall. As stated above, the motion sensors 52 may acquire PS motion data of the heart 14 at numerous map points, positioned along the walls of the various chambers during at least one cardiac cycle. Optionally, the map points may be obtained in the coronary sinus and its tributaries. Additionally or alternatively, the heart 14 may be divided into numerous map points along the walls of the various chambers.

Figure 3:
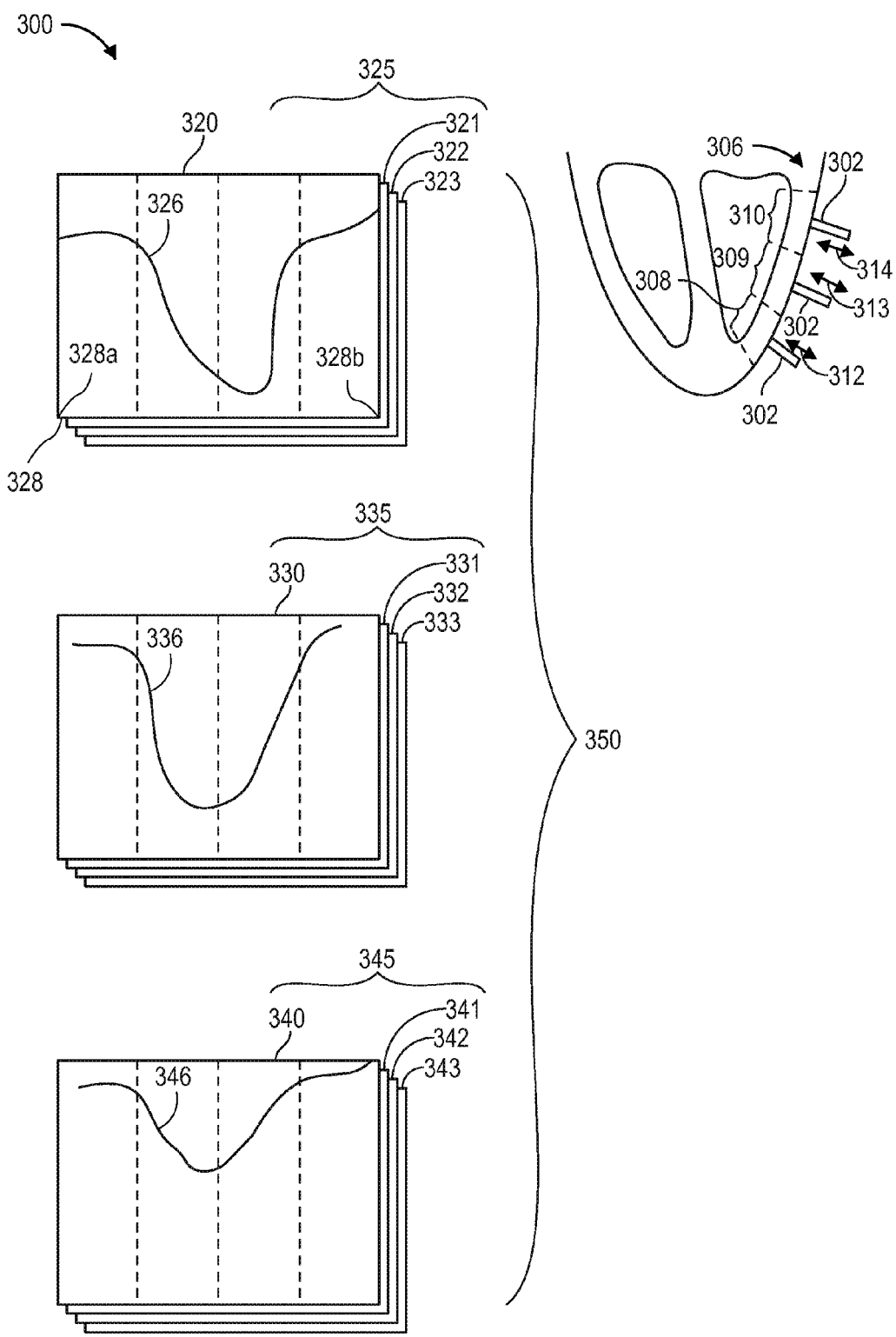
FIG. 3 illustrates an embodiment of collecting motion data using a cardiovascular navigation system exhibited by a heart.

FIG. 3 illustrates a graphical representation of a plurality of map points associated with a portion of a heart 300, such as a heart wall 306, for which it is desirable to measure PS motion data. The term "point specific" is used to indicate that the motion data is associated with a single select location on the heart wall. The data values represent positions of the single select location over one or more cardiac cycles. The heart wall 306 may be separated or divided into map points 308-310. The example of FIG. 3 shows three map points of interest 308-310 along the wall of the left ventricle. Optionally, more or fewer map points of interest may be designated. A tool 302 (e.g., the medical tool 16 with the plurality of electrophysiology sensors 52) is positioned directly against the heart wall 306 at one or more points within each map point of interest 308-310. The tool 302 tracks and measures movement of the one or more points over a select period of time. In the example of FIG. 3, the tool 302 is shown positioned against a point of interest in each map point 308-310 at different points in time.

For example, the tool 302 is positioned, during a first measuring operation, at a point within the map point 308 while collecting PS motion data associated with movement (e.g., along the arrow 312) by the map point 308. The movement may be in various linear, transverse, or rotational directions. Next, the tool 302 may be positioned, during a second measuring operation, at a point within the map point 309 while collecting PS motion data associated with movement (e.g., along the arrow 313) by the map point 309. Next, the tool 302 is positioned, during a third measuring operation, at a point within the map point 310 while collecting PS motion data associated with movement (e.g., along the arrow 314) by the map point 310.

The position of the tool 302 may be continuously monitored by a navigation system (e.g., the navigation system 20) to obtain sets of motion data associated with each map point 308-310 over a select period of time, such as, during at least one cardiac cycle. In FIG. 3, a motion waveform subset 320 is collected during one cardiac cycle while the tool 302 is held against the LV wall acquiring PS motion data for a point within the map point 308. The PS motion data may define a motion waveform 326 at the map point 308. The motion waveform 326 may represent a three dimensional (3D) trajectory, such as a position or displacement, of the map point 308. Additionally or alternatively, the 3D trajectory may represent an amount of motion and/or direction of the map point 308 over the cardiac cycle (e.g., heart heat). The motion waveform 326 is illustrated with respect to a vertical axis 327 axis representing a position or an amount of displacement of the map point 308 from a start reference position, during the cardiac cycle, illustrated along a horizontal axis 328 representing time from a beginning 328a to an end 328b of the cardiac cycle. Optionally, the tool 302 may be held against the LV wall at a point within the map point 308 for multiple heart beats or cardiac cycles thereby generating multiple motion waveform subsets 320-323 (e.g., for four consecutive heart beats). Optionally, the PS motion data subsets 320-323 may be collected for fewer than or more than four heart beats. The PS motion data subsets 320-323 associated with the map point 308 may be grouped to form a collection 325 of motion waveform subsets 320-323 associated with a single map point 308.

Once a desired amount of PS motion data is collected for the map point 308, the tool 302 is moved to a next desired position, such as at a point within the map point 309. Next, the data collection process is repeated to obtain PS motion data forming a motion waveform 336 indicative of a 3D trajectory of the map point 309 over a cardiac cycle (e.g., heart beat). Optionally, the tool 302 may be held for multiple heart beats to obtain PS motion data subsets 330-333 over a corresponding number of heart beats (e.g., cardiac cycles).

Once a desired amount of PS motion data is collected for the map point 309, the tool 302 is moved to a next desired position such as at a point within the map point 310. Next, the data collection process is repeated to obtain PS motion data forming a motion waveform 346 indicative of a 3D trajectory of the map point 310 over a cardiac cycle (e.g., heart beat). Optionally, the tool 302 may be held for multiple heart beats to obtain PS motion data subsets 340-343 over a corresponding number of heart beats (e.g., cardiac cycles). The motion waveform subsets 330-333, and 340-343, which are associated with map points 309 and 310, may be grouped to form collections 335 and 345, respectively, associated with single map points 309 and 310. The plurality of motion waveform subsets 320-343 for all map points 308-310 of interest of the heart wall 306 may collectively define a motion data set 350. Optionally, the motion data 250 that is utilized in connection with embodiments described hereafter may include information indicative of a radial component of wall movement, or may include information indicative of a longitudinal component of wall movement. Optionally, the motion data may include information associated with 3-dimensional movement calculated as a 3-D distance from an initial position at a select starting time point, such as the R wave or other global or local electrical activation time.

Optionally, more map points of the heart wall 306 may be studied to collect additional motion waveform subsets of motion data. For example, the walls of the right ventricular, right atrium, and/or left atrium may also be divided into map points, for which motion data is collected.

Figure 4A:
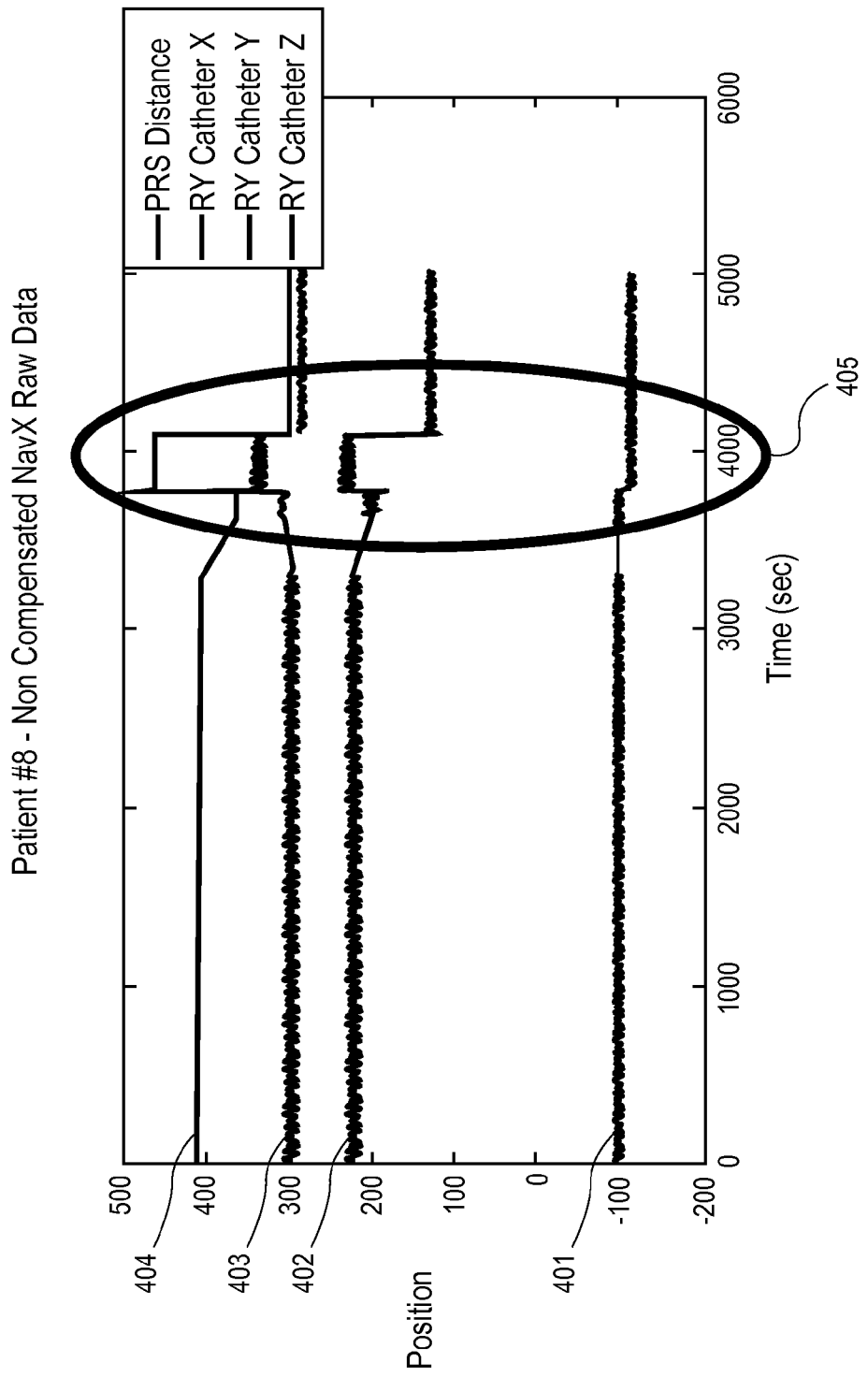
FIG. 4a illustrates a timing diagram showing raw positional data.

At 208, the method compensates and adjusts instantaneous position data of the motion sensor (e.g., motion sensors 52). The position measurements of the motion sensor may include the movement of the patient or the C-arm support structure 28 during the procedure. FIG. 4a illustrates position outputs 401, 402, and 403 from the motion sensor. Each position output 401-403 represents an instantaneous or raw position measurement from three channels (e.g., representing a Cartesian coordinate, X, Y, and Z, respectively) of the motion sensor over time. A position output 404 represents an instantaneous or raw position measurement of a patient reference sensor over time. At 405, a position spike is measured by all three channels of the motion sensor (401, 402 and 403) and the patient reference sensor 404. The position spike may represent the patient 12 moving while on the operation table 34, a change in the orientation of the C-arm support structure 28, or the like. The position data of 401-403 are compensated, for example, by the ECU 26. ECU 26 may filter out the effects of the position spike to accurately reflect the position of the region of interest.

For example, the ECU 26 may transform the raw position data 401-403 received by the motion sensor, the patient reference sensor, and the imaging system 18 by using equation 1 below.

$$\text{Compensated\_Position}_{sensor} = (\text{Position}_{sensor} - \text{Position}_{PRS}) * (\text{Orientation}_{PRS}) * (\text{Orientation}_{PRS}^{reference}) \quad \text{(Equation 1)}$$

Figure 4B:
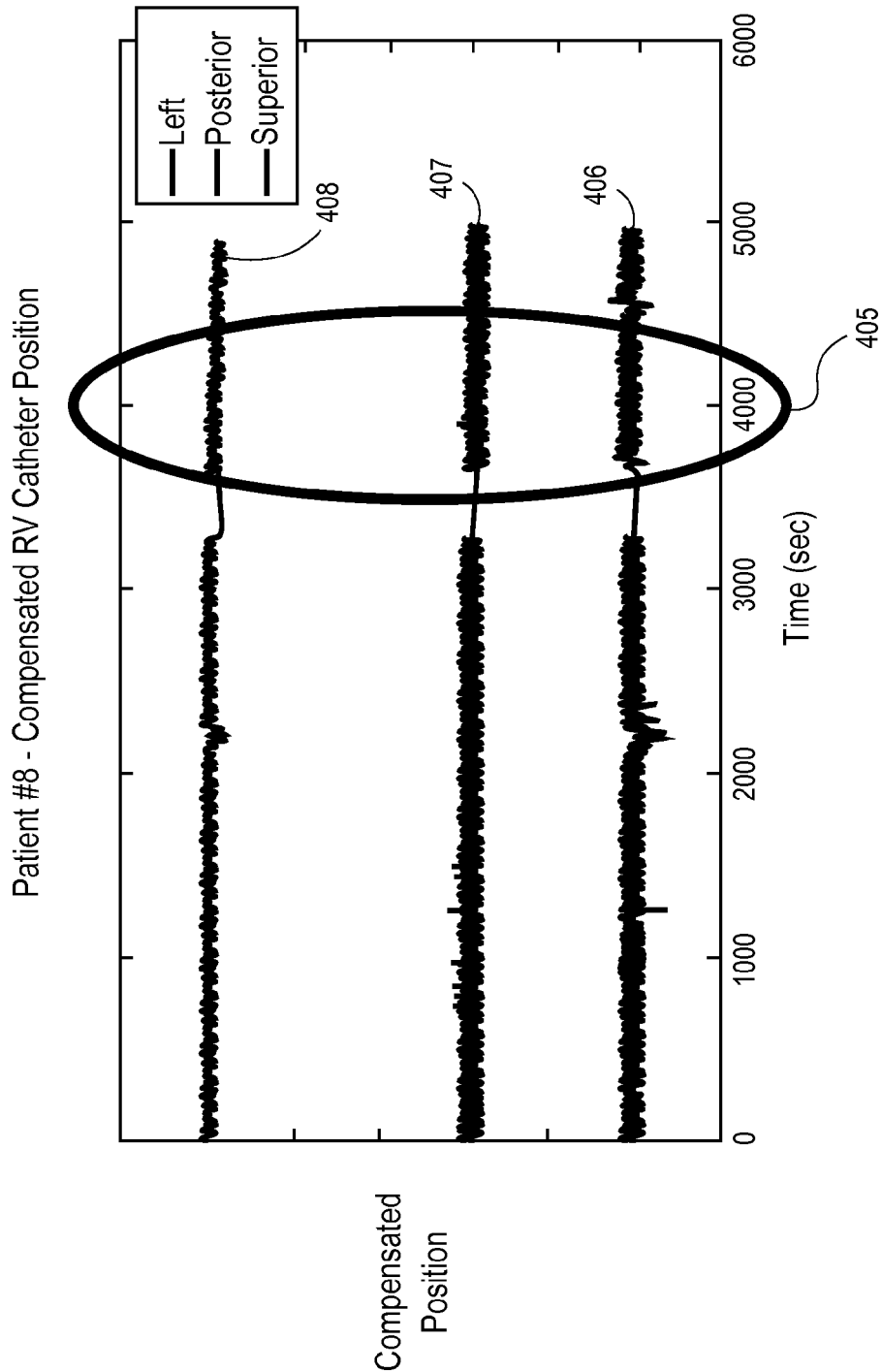
FIG. 4b illustrates a timing diagram showing compensated positional data.

The variable $\text{Position}_{sensor}$, of equation 1, represents the instantaneous raw position data (e.g., 401-403) of the motion sensor. The variable, $\text{Position}_{PRS}$, represents the instantaneous raw position data of the patient reference sensor (e.g., 404). $\text{Orientation}_{PRS}$ represents the instantaneous orientation of the patient reference sensor relative to, for example, the C-arm support structure 28 or transmitter assembly 50. $\text{Orientation}_{PRS}^{reference}$ represents the reference orientation matrix determined at 204. Thus, for example, the ECU 26 may compensate the position measurement of the motion sensor position data for the position spike 405 represented by variable $\text{Compensated\_Position}_{sensor}$ by first subtracting the position data of the patient reference sensor (e.g., 404) from the position data of the motion sensors, and then multiplying by two orientation matrices. $\text{Orientation}_{PRS}$ and Orientation$_{PRS}^{reference}$. FIG. 4b illustrates the result of applying the compensation from equation 1 to the raw motion sensor position measurements by determining a compensated motion sensor measurement shown as 406-408.

Optionally, the ECU 26 may apply additional filtering to the compensated motion sensor measurements by adjusting for additional movements, such as, movements caused by the respiratory cycle or breathing of the patient 12. For example, the measurements of the motion sensor (e.g., motion sensors 52), when placed on the heart 14, may superimpose the periodic motion induced by the respiratory cycle onto the isolated cardiac motion signal of the heart 14. The respiratory and cardiac motion exhibit distinct frequency ranges, which allow the ECU 26 to filter the effects of the respiratory motion using a band-stop or high-pass filter in the range of the patient-specific respiratory frequency to eliminate the respiratory contribution from the signal and extract the cardiac motion signal. The respiratory frequencies of the patient 12 may be measured in pre-recorded patient data using manual measurements or via an automatic frequency power spectrum analysis to exactly define the range of respiratory frequencies in the patient 12. A user may input the respiratory frequencies into the ECU 26 which may apply a patient-specific band-stop or high-pass filter to the compensated motion sensor measurement, thus excluding the patient-specific respiratory frequencies from the compensated electrophysiological measurements.

Additionally or alternatively, an internal reference sensor may be placed in a position inside the patient 12 which is only affected by the respiratory motion of the patient. The ECU 26 may receive the measurements of the internal reference and subtract them from the compensated motion sensor measurements to determine motion sensor measurements unaffected by the respiratory motion of the patient.

At 210, the method 200 determines a normalization time based on an electrical signal. As described above, the tool 302 (e.g., motion sensor, the motion sensor 52) measures the position of different locations or map points of the region of interest, such as the heart 14. However, for example, the measurements at each map point or the same map point may occur at different cardiac cycles resulting in a set of asynchronous waveforms. Each cardiac cycle can be time-synchronized by the ECU 26, to compare PS motion data at the same or at different map points, using a reference electrical signal such as a global or local electrical signal to define the timing of a cardiac cycle. The global electrical signal may be a surface ECG signal or an IEGM signal from a stationary tool at the right ventricular (RV) apex, or a local electrical signal such as the bipolar IEGM from the medical tool 16, or the like.

Figure 5:
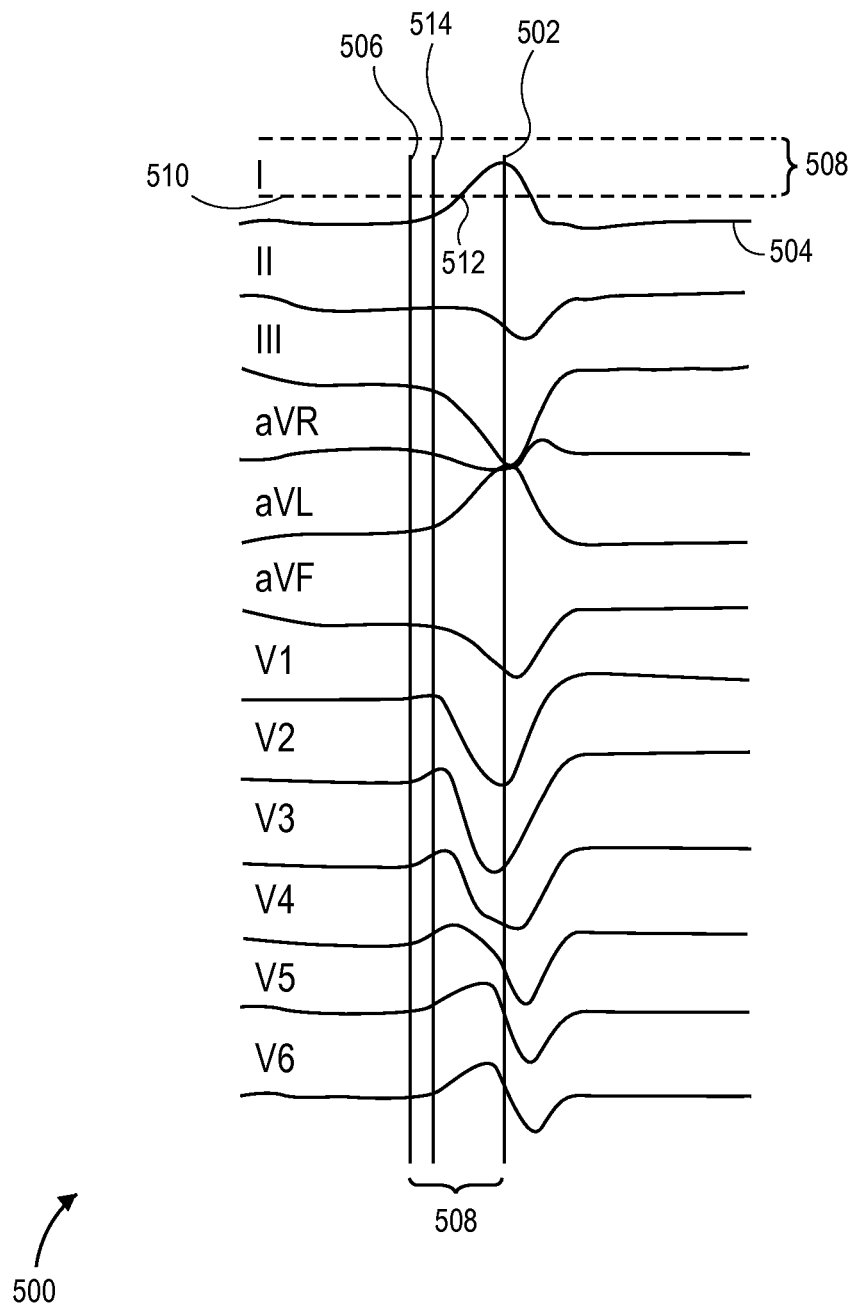
FIG. 5 illustrates an electric signal received by an electronic control unit, in accordance with an embodiment.

FIG. 5 is a graphical representation 500 of the electrical signal over time received by the ECU 26. The electrical signal or data is shown from a 12-lead surface ECG. It should be noted that the electrical signal may be any global electrical signal measuring the electrical behavior of a given beat, for example, an IEGM (intracardial electrogram) signal from a stationary tool near the region of interest (e.g., the right ventrical apex), a bipolar IEGM from the medical tool (e.g., catheter), or the like.

The ECU 26 determines a normalization time 508 or the time of the earliest electrical activation anywhere in the heart by calculating the difference between a reference peak 502 of a reference electrical signal 504 (e.g., lead I of the surface ECG), and an earliest onset 506 on all 12-lead surface ECG signals.

Optionally, the normalization time may be based on the difference between a predetermined percentage of a cycle length (e.g., 20%) 514 from the reference peak 502 (e.g., R-peak). The predetermined cycle length 514 may be used for each individual map point and/or group of map points. Additionally or alternatively, the predetermined cycle length 514 may be an average, maximum, minimum, or other combination of cycle lengths of the plurality of map points with PS motion data.

The reference electrical signal 504 may include invalid beats such as ectopic beats (e.g., based on the waveform shape, amplitude, timing, duration, and the like). Ectopic beat represents a disturbance of the cardiac rhythm in which the beat arises outside the region of the heart muscle ordinarily responsible for impulse formation. The ectopic beats may have a lower or higher peak amplitude relative to a normal R-wave amplitude of a normal ORS complex which is used as the peak to define the normalization time.

To locate the reference peak 502 in the reference electrical signal 504, the ECU 26 may compare the reference electrical signal 504 against a pre-determined threshold amplitude 510 and a minimum time distance between two consecutive peaks (e.g., 800 ms). The ECU 26 may determine that a sample point above the threshold amplitude 510 defines peaks as a first instance 512 of a change in slope from positive to zero or negative in a consecutive series of sample points. Thus, the ECU 26 may detect the peak 502 of the R-wave on all beats to be used to calculate the normalization time 508.

The ECU 26 may identify ectopic beats, which are not used to calculate the normalization time 508, using a threshold amplitude bandwidth 508 of the electrical sensor measurements. For example, the ECU 26 may determine that the reference electrical signal 504 has a normal R-wave amplitude if the reference peak 502 of the reference electrical signal 404 is within the threshold amplitude bandwidth 508. If the reference electrical signal 504 includes a peak 502 over or not within the threshold amplitude bandwidth 508 the ECU 26 may determine that the peak 502 of the reference electrical signal 404 as an ectopic beat. Further, the ECU 26 may exclude the immediate neighbors of an ectopic beat (e.g., 305) to ensure that ectopic beats which can affect cardiac biomechanics for a couple of cycles do not introduce variability in the motion data.

Once the ECU 26 determines the normalization time, a motion waveform of a map point (e.g., 308-310) may be determined by comparing the position data of the compensated motion sensor at the instantaneous position against the position at the normalization time.

Optionally, the method 200 may determine an ensemble average motion waveform. The ensemble average motion waveform may represent multiple motion waveforms of a map point that correspond to different cardiac cycles. For example, the ensemble average motion waveform may be an average motion characterization waveform as disclosed in U.S. provisional application Ser. No. 61/906,305, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION", which is expressly incorporated herein by reference in its entirety.

Optionally, the method 200 may include applying a rotation technique to the motion waveform (e.g., the motion waveform 326, 336, 346) to correct for non-periodicity. The ECU may apply the rotation technique on each individual cardiac cycle or on the ensemble averaged motion waveforms. A periodic motion waveform (e.g., the motion waveform 326, 336, 346) of a map point (e.g., 308-310) during a cardiac cycle has at the normalization time and at the end of the cardiac cycle approximately the same measured displacement or position. Non-periodicity of the motion waveform may occur from errors in the acquired PS motion data for the map point that defines the motion waveform. The non-periodic behavior may be due to, for example, measurement error of the motion sensor (e.g., the motion sensors 52) or the patient reference sensor, shifts in the position of the medical tool 16 during cardiac cycles, gradual changes in respiratory frequencies, or the like. To correct for this non-periodicity, the ECU 26 may apply the rotation technique to the motion waveform. The rotation technique shifts the motion waveform from a set reference or first anchor point to a second anchor point at the end of the cardiac cycle using. The shift of the motion waveform may be, for example, a linear scale such that the amount of shift of the motion waveform increases approaching the end of the motion waveform at the end of the cardiac cycle.

Figure 6:
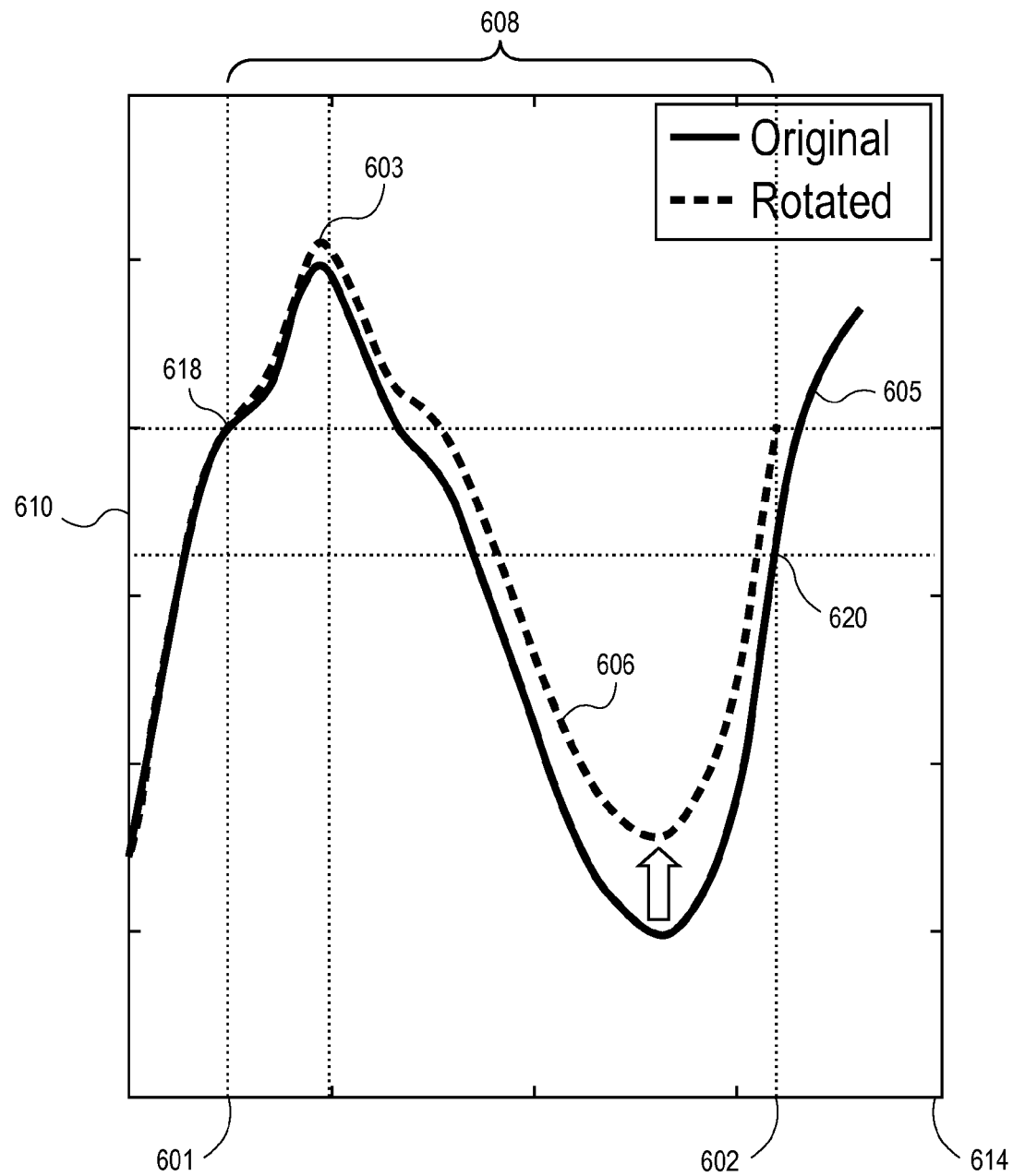
FIG. 6 illustrates a motion waveform, in accordance with an embodiment herein.

FIG. 6 illustrates a motion waveform 605 (e.g., motion waveform 326) defined by PS motion data acquired at a map point. The motion waveform 605 may represent a displacement of the map point with respect to a vertical axis 610, representing an amount of displacement of the map point, during a cardiac cycle 608 along a horizontal axis 614. At a normalization time 601 the motion waveform 605 has a measured displacement at 618. At an end 602 of the cardiac cycle 608, the motion waveform 605 has a measured displacement at 620. The difference in the displacements of the motion waveform 605 at the normalization time 601 and the end 602 of the cardiac cycle 608 shows that the motion waveform 605 is non-periodic. The ECU 26 applies the rotation technique to generate a rotated motion waveform 606 that results in a periodic motion waveform. The reference or first anchor point may be the normalization time 601. It should be noted, another time point may be used, such as the peak reference 603 of the motion waveform 605. The second anchor is at the end 602 of the cardiac cycle 608.

The ECU 26 rotates or shifts the motion waveform 605 at the first anchor 601, linearly increasing the shifting magnitude until the second anchor 602 has a displacement value of 618 or equal to the first anchor 601 resulting in the rotated motion waveform 606.

The navigation system 20, may determine a Cartesian coordinate system (e.g., (X, Y, Z)) representing the position measurements from the motion sensor (e.g., the motion sensor 52), the imaging system 18, and the patient reference sensors having a predetermined reference as the origin, such as the operation table 34 or the patient reference sensors. Optionally, the position measurements may be converted using a matrix translation and rotation operation to a cardiac coordinate system which is described with respect to radial, longitudinal, and circumferential directions of the left ventricular (LV).

Figure 7:
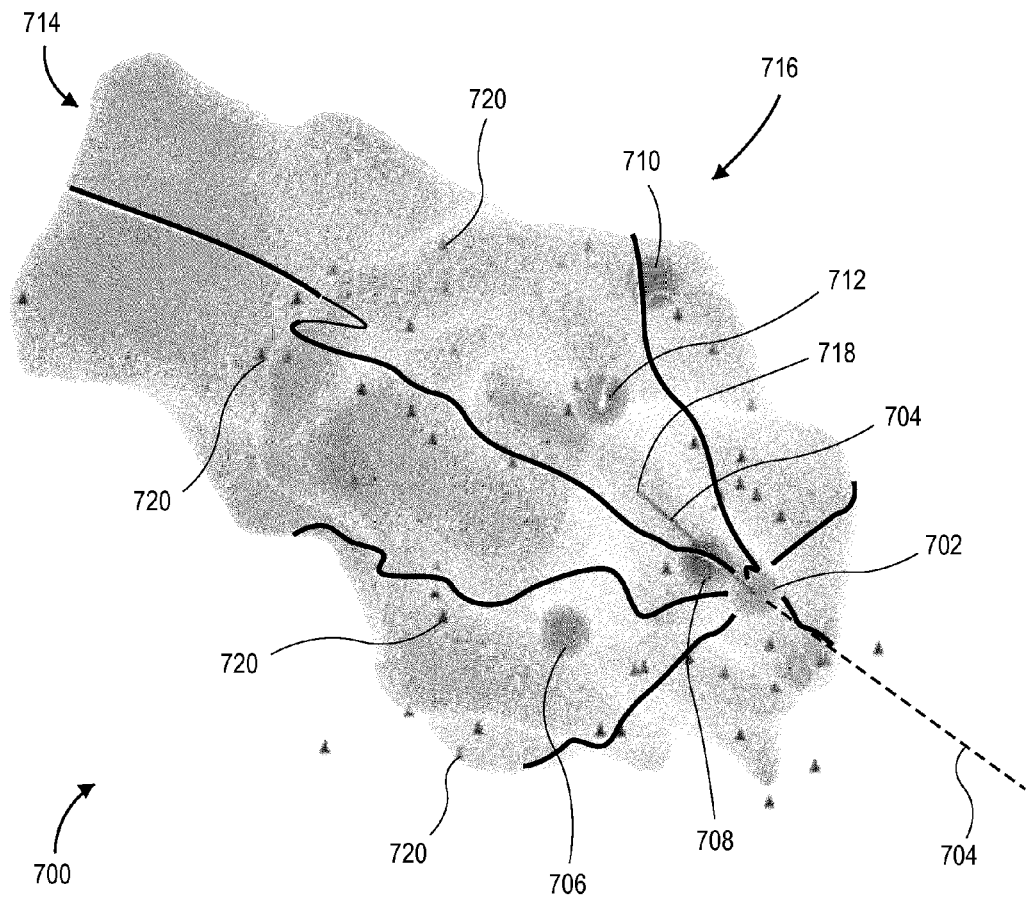
FIG. 7 illustrates a cardiac coordinate system based on a patient, in accordance with an embodiment herein

FIG. 7 is a 3D visualization 700 of a cardiac coordinate system based on a plurality of map points 720. The ECU 26 may determine a long axis 704 of the LV in which an operator (e.g., Doctor, clinician) indicates an apex 702 of the LV and a base 714 of the mitral valve in each patient intra-operatively using fluoroscopy images or the electro-anatomical map from the image system 18 via the operator system interface 54. Once the operator indicates the apex 702, the ECU 26 records a time stamp. The operator then defines the mitral annulus 716 using at least four equally spaced markers 706-712 around the circumference of the mitral annulus 716. The ECU 26 determines the position at each of the markers 706-712, the apex 702, and the base 714 to obtain the three dimensional (3D) position of the patient-specific anatomical markers. The long axis 704 of the LV is then defined as a line connecting the apical point (e.g., apex 702) to centroid 718 of the mitral annulus points 706-712.

Additionally or alternatively, the ECU 26 may perform an automatic segmentation based on the plurality of map points 720 as disclosed in U.S. patent application titled "METHOD AND SYSTEM TO AUTOMATICALLY ASSIGN MAP POINTS TO ANATOMICAL SEGMENTS" having U.S. patent application Ser. No. 14/304,615, filed Jun. 1, 2014, which is expressly incorporated herein by reference in its entirety.

Once the long axis 704 of the LV is determined, the ECU 26 converts the Cartesian coordinates of the position measurements of the motion sensor, the patient reference sensors, and/or the image system 18 to a cylindrical cardiac coordinate system by first determining a parallel vector (W) using equation 2. Wherein, the variable Z is the longitudinal unit vector from the apex 702 to the mitral annulus centroid 718. V is a new unit vector that is in the direction of the minimum non-zero component of Z. Once the parallel vector is determined, the ECU 26 will determine a new unit vector, X, that is perpendicular to the longitudinal vector shown in equation 3, and determine a new unit vector, Y, that is a cross-product of X and Z shown in equation 4.

$$\vec{W} = (\vec{Z} \cdot \vec{V})\vec{Z} \quad \text{(Equation 2)}$$

$$\vec{X} = (\vec{V} - \vec{W}) \quad \text{(Equation 3)}$$

$$\vec{Y} = \vec{X} \times \vec{Z}) \quad \text{(Equation 4)}$$

Once the unit vectors are determined, the ECU 26 may determine the cylindrical cardiac coordinates (radial, circumferential, longitudinal) from the Cartesian coordinates using Equation 5 below. It should be noted that other coordinate systems may be used, for example, a polar cardiac coordinate system, or a Cartesian coordinate system based on an anatomical marker, such as, the apex 702.

$$\rho = \sqrt{x^2 + y^2}$$
$$\theta = \tan^{-1}\left(\frac{y}{x}\right)$$
$$Z = Z$$

Figure 8:
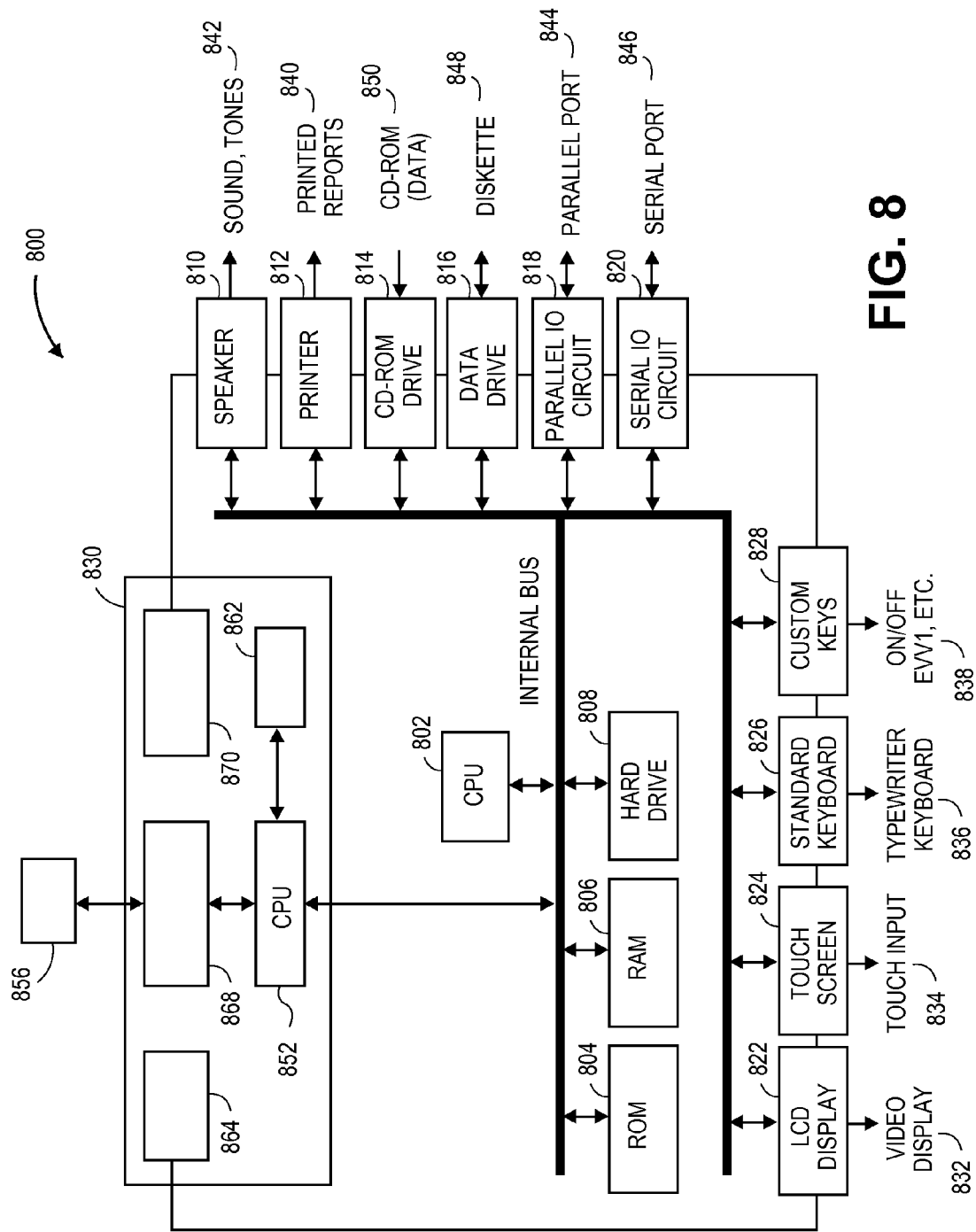
FIG. 8 illustrates a system for analyzing motion data, in accordance with an embodiment.

FIG. 8 illustrates a functional block diagram of a navigation system 800 that is operated in accordance with the processes described herein to analyze motion and electrical data and to interface with a medical tool 856 (e.g., the medical tool 16). The navigation system 800 includes an internal bus that connects/interfaces with a Central Processing Unit (CPU) 802, ROM 804, RAM 806, a hard drive 808, the speaker 810, a printer 812, a CD-ROM drive 814, a floppy drive 816, a parallel I/O circuit 818, a serial I/O circuit 820, the display 822, a touch screen 824, a standard keyboard connection 826, custom keys 828, and an electronic control unit (ECU) 830. The internal bus is an address/data bus that transfers information between the various components described herein. The hard drive 808 may store operational programs as well as data, such as waveform templates, detection thresholds, and PS motion data.

The CPU 802 typically includes a microprocessor, a microcontroller, or equivalent control circuitry, designed specifically to control interfacing with the navigation system 800, an imaging system (e.g., imaging system 18), the medical tool 856, an operation table (e.g., the operation table 34), or the like. The CPU 802 may include RAM or ROM memory, logic and timing circuitry, state machine circuitry, and I/O circuitry to interface with the different components of the navigation system 800. The display 822 (e.g., the display 58) may be connected to a video display 832. The touch screen 824 may display a graphic user interface corresponding to the operator system interface 54 allowing a user (e.g., a clinician, doctor) to control the navigation system 200. The display 822 may display various information related to the processes described herein. The touch screen 824 accepts a user's touch input 834 when selections are made. The keyboard 826 (e.g., a typewriter keyboard 836) allows the user to enter data to the displayed fields, as well as interface with the ECU 830. Furthermore, custom keys 828 turn on/off 838 the navigation system 800. The navigation system 800 may communicate with a printer 812 that prints copies of reports and/or images 840 (e.g., 3D visualizations of the region of interest) for a physician to review or to be placed in a patient file, and speaker 810 provides an audible warning (e.g., sounds and tones 842) to the user. The parallel I/O circuit 818 interfaces with a parallel port 844. The serial I/O circuit 820 interfaces with a serial port 846. The floppy drive 816 accepts diskettes 848. Optionally, the floppy drive 816 may include a USB port or other interface capable of communicating with a USB device such as a memory stick. The CD-ROM drive 814 accepts CD ROMs 850.

A CPU 852 of the ECU 830 is configured to analyze motion characterization data and electrical measurement data collected by the cardiovascular navigation system to identify electrical and motion characterization data exhibited by a heart. Optionally, the CPU 852 may be integrated with the CPU 802. The CPU 852 receives PS motion data, as explained herein. Further, the CPU 852 includes a PS motion data analysis circuit module 862 that defines motion waveforms from the PS motion data and may convert PS motion data to a cardiac coordinate system, as explained herein.

The CPU 852 includes an electrical waveform analysis circuit module 864 that analyzes the reference electrical signal and determines a motion waveform by calculating the normalization time based on the reference electrical signal and the compensated motion data from a position analysis circuit module 868.

The position analysis circuit module 868 measures the orientation position of the PRS to a reference, such as the transformer assembly 50. Further, the position analysis circuit module 868 analyzes the position measurement of the heart based on the motion sensor. The position analysis circuit module 868 determines the orientation matrix and compensates and adjusts the position data from the motion sensor based on the measurements from the PRS.

The CPU 852 may also include a rotation circuit module (RCM) 870. The RCM 870 receives the motion waveform from the electrical waveform analysis module 864 and applies the rotation technique to determine a rotated motion waveform. The display 822 displays the rotated motion waveform based on the calculations of the RCM 870.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method to measure cardiac motion using a cardiovascular navigation system, the method comprising:
    positioning a patient reference sensor (PRS) on a patient, wherein the PRS may determine a position of the patient relative to a reference point;
    determining a reference orientation matrix based on an orientation of the PRS relative to the reference point;
    determining a normalization time based on an electrical signal;
    obtaining point specific (PS) motion data for a plurality of map points, wherein the PS motion data indicates a three dimensional trajectory at the corresponding map point on a wall of a heart of the patient during at least one cardiac cycle; and
    compensating the PS motion data based on the PRS.

2. The method of claim 1, further comprising applying a rotation technique to a motion waveform for the corresponding map point based on the normalization time, wherein the motion waveform is defined by the PS motion data.

3. The method of claim 2, wherein the motion waveform is an ensemble average based on PS motion data obtained during a plurality of cardiac cycles.

4. The method of claim 1, further comprising converting the PS motion data into a cardiac coordinate system based on the patient.

5. The method of claim 1, further applying a high-pass or band-stop filter to the PS motion data based on a respiratory frequency of the patient.

6. The method of claim 1, wherein the electrical signal is one or a subset of a 12-lead surface ECG from the patient.

7. The method of claim 1, wherein the PS motion data is obtained by a motion or an electrophysiological sensor.

8. The method of claim 1, wherein the compensating operation is further based on an instantaneous position and orientation of the PRS relative to the reference point, and the reference orientation matrix.

9. The method of claim 1, wherein the reference point is based on a C-arm support structure of an imaging system.

10. The method of claim 1, wherein the compensating operation is further based on a respiratory frequency of the patient.

11. The method of claim 1, wherein the normalization time is based on a peak of the electric signal and at least one of an earliest global electrical activation or a predetermined percentage of a cycle length.

12. A system for measuring cardiac motion comprising:
    a patient reference sensor (PRS) configured to determine a position of a patient relative to a reference point;
    a motion sensor configured to obtain point specific (PS) motion data for a plurality of map points, wherein the PS motion data indicates a three dimensional trajectory at the corresponding map point on a wall of a heart of the patient during at least one cardiac cycle;
    an input configured to receive the position measurements of the PRS and the motion sensor; and
    a processor configured to:
        determine a reference orientation matrix based on an orientation of the PRS relative to the reference point;
        determine a normalization time based on an electrical signal; and
        compensate the PS motion data based on the PRS.

13. The system of claim 12, wherein the processor is further configured to apply a rotation technique to a motion waveform for the corresponding map point based on the normalization time, wherein the motion waveform is defined by the PS motion data.

14. The method of claim 13, wherein the motion waveform is an ensemble average based on PS motion data obtained during a plurality of cardiac cycles.

15. The system of claim 12, wherein the processor is further configured to convert the PS motion data into a cardiac coordinate system based on the patient.

16. The system of claim 12, wherein the processors is further configured to apply a high-pass or band-stop filter to the PS motion data based on a respiratory frequency of the patient.

17. The system of claim 12, further comprising an imaging system with a C-arm support structure, wherein the reference point is based on the C-arm support structure.

18. The system of claim 12, wherein the normalization time is based on a peak of the electric signal and at least one of an earliest global electrical activation or a predetermined percentage of a cycle length.

19. The system of claim 12, wherein the compensation operation by the processor is further based on an instantaneous position and orientation of the PRS relative to the reference point, and the reference orientation matrix.

20. The system of claim 12, wherein the compensation operation by the processor is further based on a respiratory frequency of the patient.

* * * * *